United States Patent [19]

Fusco

[11] 4,178,242

[45] Dec. 11, 1979

[54] METHOD FOR THE PURIFICATION OF SEWAGE WATERS WHICH CONTAIN ORGANIC COMPOUNDS OF AN ANIONIC CHARACTER

[75] Inventor: Raffaello Fusco, Milan, Italy

[73] Assignee: Anic S.p.A., Palermo, Italy

[21] Appl. No.: 935,098

[22] Filed: Aug. 21, 1978

Related U.S. Application Data

[63] Continuation of Ser. No. 734,189, Oct. 20, 1976, abandoned.

[30] Foreign Application Priority Data

Nov. 11, 1975 [IT] Italy .............................. 29190 A/75

[51] Int. Cl.$^2$ ............................................... C02B 1/20
[52] U.S. Cl. .................................................... 210/54
[58] Field of Search .................... 210/52, 54 C, 54 R, 210/42 R; 260/564 E

[56] References Cited

U.S. PATENT DOCUMENTS

| | | | |
|---|---|---|---|
| 2,545,876 | 3/1951 | Clemence et al. | 260/564 E |
| 2,759,973 | 8/1956 | Grogan et al. | 260/564 E |
| 3,822,205 | 7/1974 | Oohara et al. | 210/52 |

FOREIGN PATENT DOCUMENTS

| | | | |
|---|---|---|---|
| 1538328 | 7/1968 | France | 260/564 E |
| 74-05976 | 2/1974 | Japan | 210/54 C |

*Primary Examiner*—Benoit Castel
*Attorney, Agent, or Firm*—Morgan, Finnegan, Pine, Foley & Lee

[57] ABSTRACT

Bisisothiouronium salts are disclosed, which are extremely useful in the depollution of water in which the pollutants are dyestuffs and generally anionic compounds difficult to precipitate. Precipitation with bisisothiouronium salts according to the invention occurs, conversely, very easily.

1 Claim, No Drawings

METHOD FOR THE PURIFICATION OF SEWAGE WATERS WHICH CONTAIN ORGANIC COMPOUNDS OF AN ANIONIC CHARACTER

This is a continuation of application Ser. No. 734,189 filed Oct. 20, 1976, now abandoned.

This invention relates to a method for purification of sewage waters which contain organic compounds of an anionic character and to the use of bis-isothiouronium salts in the method.

It is known that many organic compounds of arionic character are found in industrial sewage waters and that often their removal is a difficult and expensive task.

It has now been surprisingly found, that certain classes of such anionic compounds can quantitatively be precipitated, or almost so, by using bis-isothiouronium salts: which form, with the above named anionic compounds, saline derivatives which are very poorly water-soluble and which can thus conveniently be eliminated.

More particularly, numerous classes of dyestuffs, having present in their molecules one or more sulphonic groups, are precipitated by the reactants of the present invention.

This property can be exploited for removing residual dyestuffs from dye baths, especially when such dyestuffs cannot be abated by conventional inorganic precipitants (such as calcium hydroxide or aluminum sulphate).

Even when conventional inorganic precipitants are efficient, it has been found that the coaction of the same with the novel reactants of this invention affords advantages, resulting in more complete purification and considerably reduces the sludge volume, so that the sludge removal is facilitated.

Another interesting property of the products contemplated by the present invention is that they furnish saline compounds, which are highly insoluble, with many anionic capillary-active agents marketed nowadays, such as alkylbenzenesulphonates, both straight chain and branched-chain, and the long-chain acidic alkyl sulphates.

Such an outstanding property can be exploited to eliminate in an insoluble form, residues of such capillary-active agents such as are present in the sewage waters of numerous industries and which are notoriously difficult to remove by biological degradation or otherwise.

It is quite obvious that the purification of sewage waters in which dyestuffs and capillary-active agents of the above mentioned kinds are present, such as the waters discharged by dyeing plants, can efficiently be achieved by the use of the products dealt with by the present invention, the additional benefit of concurrently removing other bodies which are present in a dispersed form, such as the dispersed dyestuffs, which are embedded in the precipitate also being attained.

The compounds used in the present invention are water-soluble bodies having a neutral character and are nontoxic to humans and animals in general, noncorrosive and have no odor, so that the possible presence of traces of such compounds in waters which have been clarified with the depollution treatment will not cause any damage of fish or cause any trouble whatever.

The compounds which are contemplated by the present invention are represented by the general formula:

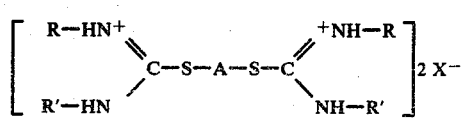

wherein
R and R' can be both hydrogen atoms or two lower alkyls (C1-C3) or R can be an alkyl, a cycloalkyl and aralkyl or an aryl and R' a hydrogen atom;
A is the residue of a linear or branched aliphatic hydrocarbon, or of an aryl-aliphatic hydrocarbon or also a residue from an aliphatic or mixed aliphatic-aromatic ether or derived thioether;
$X^-$ is an anion, such as $Cl^-$, $Br^-$, $OSO_4H^-$, $CH_3SO_3^-$ or $Ar-SO^-_3$.

By way of example, but without limitation, A can be:
$-(CH_2)_n$, with n equal to or greater than 6;

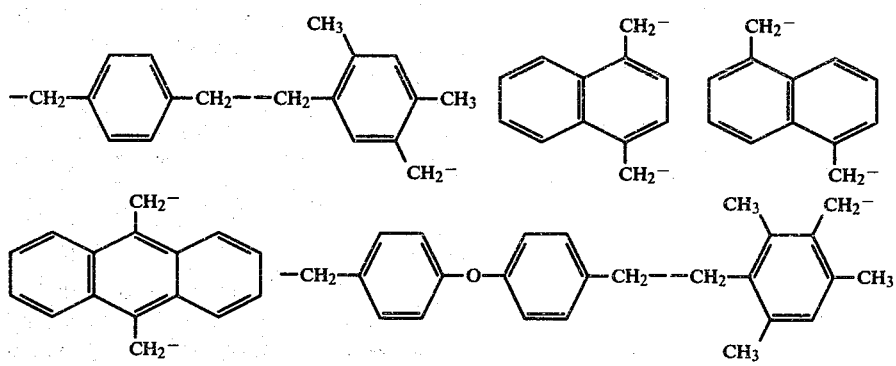

The compounds within the scope of this invention can be prepared by reacting bis-halogen derivatives of the general formula:

wherein X is Cl or Br and A has the meaning explained hereinbefore, with a thiourea having the general formula:

wherein R and R' have the meanings explained hereinabove.

As an alternative, such thioureas can be reacted with esters having the general formula:

wherein X is a group such as CH$_3$SO$_2$O—, HOSO$_2$—O, Ar—SO$_2$O—and the like.

The reaction between the two reactants can be effected in a solvent which also dissolves, at least partially, one of the reactants at temperatures which are comprised, consistently with the reaction, between the ambient temperature and the boiling point of the solvent, for a time which is long enough to complete the reaction.

Appropriate solvents are water, lower alcohols (C1–C4), simple aliphatic ketones (acetone, methylethylketone), dioxan, vicinal glycols (ethylene glycol, propylene glycol), acetonitrile and dimethyl formamide.

The solvent choice is determined by criteria of convenience, such as cost and easy recovery, reactivity of the components of the solvent itself and reaction time.

EXAMPLE 1

Bis-isothiouronium salt from 1:5-bis-chloromethyl-2:4-dimethylbenzene and thiourea 6.1 Grams of 1:5-bis chloromethyl-2:4-dimethylbenzene and 4.6 grams of thiourea in 50 mls. abs. ethanol are refluxed for 3 hours.

The bis-isothiouronium salt crystallizes on cooling on an ice bath.

Yield: 80%. Melting point 240° C. (approx.)

EXAMPLE 2

Bis-isothiouronium salt from bis-chloromethylnaphthalene and thiourea 9.5 Grams of a mixture of bis-chloromethylnaphthalenes, which contain monochloromethylnaphthalenes as impurities, and 6.4 grams of thiourea in 50 mls. of Abs. ethanol are refluxed for 3 hours. The mixture is allowed to cool to complete the crystallization of the bis-isothiouronium salt.

Yield: 65%. Melting point 260° C. (approx. dec.)

EXAMPLE 3

Bis-isothiouronium salt from 9:10-bis-chloromethylanthracene and thiourea 8.3 Grams of 9:10-bis-chloromethylanthracene and 5 grams of thiourea in 100 mls dioxan are refluxed for one hour. The mixture is allowed to cool in order to complete the crystallization of the bis-isothiouronium salt.

Yield: 90%. Melting point 245° C.–250° C. (dec.)

EXAMPLE 4

Bis-isothiouronium salt from 4:4'-bis-chloromethyldiphenylether and thiourea 11.2 Grams of 4:4'-bis-chloromethyldiphenylether and 6.4 grams of thiourea in 70 mls abs. ethanol are refluxed for 3 hours. The mixture is allowed to cool in order to complete the crystallization of the bis-isothiouronium salt.

Yield: 75%. Melting point 212° C.–215° C.

EXAMPLE 5

Bis-isothiouronium salt from 1:4-bis-chloromethylbenzene and thiourea 17.5 Grams of 1:4-bischloromethylbenzene and 15.3 grams of thiourea in 150 mls. abs. ethanol are refluxed for 3 hours. The mixture is allowed to cool in order to complete the crystallization of the bis-isothiouronium salt.

Yield: 91%. Melting point 250° C. approx.

EXAMPLE 6

Bis-isothiouronium salt from 1:6-dibromohexane and thiourea

11 Grams of 1:6-dibromohexane and 6.9 grams of thiourea in 50 mls. abs. ethanol are refluxed for 3 hours. The bis-isothiouronium salt crystallizes on cooling on an ice bath.

Yield: 93%. Melting point 197° C.–198° C.

EXAMPLE 7

Bis-isothiouronium salt from 1:10-dibromodecane and thiourea 13.5 Grams of 1:10-dibromodecane and 6.9 grams of thiourea in 50 mls. abs. ethanol are refluxed for 3 hours. The bis-isothiouronium salt crystallizes by cooling on an ice bath.

Yield: 83%. Melting point 156° C.–158° C.

EXAMPLE 8

Bis-isothiouronium salt from 1:5-bis-chloromethyl-2:4-dimethylbenzene and phenylthiourea 6.1 Grams of 1:5-bischloromethyl-2:4-dimethylbenzene and 9.2 grams of phenylthiourea in 50 mls. abs. ethanol are refluxed for 3 hours. The alcoholic solution is evaporated and taken up with ethyl acetate, the bis-isothiouronium salt being obtained.

Yield: 92%. Melting point 175° C.–180° C.

EXAMPLE 9

Bis-isothiouronium salt from 1:6-dibromohexane and phenylthiourea 7.6 Grams of 1:6-dibromohexane and 9.4 grams of phenylthiourea in 50 mls. abs. ethanol are refluxed for 3 hours. The bis-isothiouronium salt crystallizes by cooling on an ice bath.

Yield: 79%. Melting point 194° C.–196° C.

EXAMPLE 10

Bis-isothiouronium salt from 1:10-dibromodecane and phenylthiourea.

6.7 Grams of 1:10-dibromodecane and 6.8 grams of phenylthiourea in 50 mls. abs. ethanol are refluxed for 3 hours. The alcoholic solution is evaporated and taken up with ethyl acetate, the bis-isothiouronium salt being obtained.

Yield: 90%. The product has a rubbery consistency.

EXAMPLE 11

Bis-isothiouronium salt from 1:4-bis-chloromethylbenzene and phenylthiourea 2.6 Grams of 1:4-bis-chloromethylbenzene and 4.6 grams of phenylthiourea in 30 mls. of abs. ethanol are refluxed for 3 hours. The bis-isothiouronium salt crystallizes upon cooling on an ice bath.

Yield: 93%. Melting point 212° C.–213° C.

EXAMPLE 12

Bis-isothiouronium salt from 1:5-bis-chloromethyl-2:4-dimethylbenzene and methylthiourea 6.1 Grams of 1:5-bis-chloromethyl-2:4-dimethylbenzene and 5 grams of methylthiourea in 50 mls. abs. ethanol are refluxed for 3 hours. The alcoholic solution is evaporated and taken up with ethyl acetate, the bis-isothiouronium salt being obtained.

Yield: 95%. Melting point 110° C. (approx.)

EXAMPLE 13

Bis-isothiouronium salt from 1:5-bis-chloromethyl-2:4-dimethylbenzene and N,N'-dimethylthiourea 6.1 Grams of 1:5-bis-chloromethyl-2:4-dimethylbenzene and 6.2 grams of N,N'-dimethylthiourea in 50 mls abs. ethanol are refluxed for 3 hours. The alcoholic solution is evaporated and taken up with ethyl acetate, the bis-isothiouronium salt being obtained.

Yield: 82%. Melting point 98° C.–105° C.

EXAMPLE 14

Bis-isothiouronium salt from 1:5-bis-chloromethyl-2:4-dimethylbenzene and cyclohexylthiourea 6.1 Grams of 1:5-bis-chloromethyl-2:4-dimethylbenzene and 9.5 grams of cyclohexylthiourea in 50 mls. abs. ethanol are refluxed for 3 hours. The alcoholic solution is evaporated and taken up with ethyl acetate, the bis-isothiouronium salt being obtained.

Yield: 96%. Melting point 197° C.–200° C.

EXAMPLE 15

Bis-isothiouronium salt from 1:4-bis-chloromethylbenzene and cyclohexythiourea 5.2 Grams of 1:4-bis-chloromethylbenzene and 9.5 grams of cyclohexylthiourea in 50 mls. abs. ethanol ar refluxed for 3 hours. The alcoholic solution is evaporated and taken up with ethyl acetate, the bis-isothiouronium salt being obtained.

Yield: 95%. Melting point 185° C.–190° C.

EXAMPLE 16

Example of purification

To 4,000 liters of sewage water from a dyeing and washing bath containing 1.26 kilograms of Orange Procion MX 2R, 1.11 kgs of Yellow Lavafix EG, 0.09 kgs. of Red Lavafix E 4D, 1 kg. of nonionic capillary active substance, 1 kg. of sulphonated lauryl alcohol, 80 kgs. of $Na_2SO_4$ and 21 kgs. of $Na_2CO_3$, adjusted to a pH of 7 by $H_2SO_4$, is added a solution of 4 kgs. of the isothiouronium salt of Example 2.

The liquor is allowed to settle for 30 minutes. A sample of the supernatant liquid is diluted with water at 1:20, and when observed through a thickness of 10 centimeters is colorless.

EXAMPLE 17

Examples of purification

To samples of 100 mls each of the sewage water of Example 16, adjusted to a pH of 7, are added solutions of 10 grams per liter of the isothiouronium salt as per the several Examples above.

The results ae tabulated in the following Table:

| Isothiouronium salt used, as per Example | Mls. solution used | Diluted at 1:10 with Water |
|---|---|---|
| 1 | 10 | very little colored[a] |
| 4 | 10 | colorless |
| 5 | 10 | little colored[a] |
| 7 | 10 | colorless |
| 9 | 15 | colorless |
| 11 | 12 | colorless |
| 14 | 10 | colorless |

[a]Further additions of the solution of the isothiouronium salt do not improve the decoloration of the supernatant liquor.

What I claim is:

1. A method for the purification of sewage waters containing anionic organic compounds comprising the steps of adding to said water compounds having the general formula:

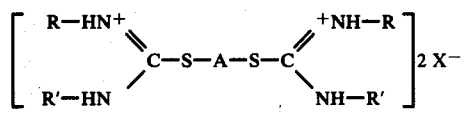

wherein R and R' are hydrogen atoms or to lower alkyl groups ($C_1$–$C_3$), or R is an alkyl group, a cycloalkyl group, an aralkyl group or an aryl group and R' a hydrogen atom, A is the residue of an aliphatic linear or branched hydrocarbon, or of an arylaliphatic hydrocarbon, or a residue derived from an aliphatic or mixed aliphatic-aromatic ether or thioether, $X^-$ is an anion such as $Cl^-$, $Br^-$, $OSO_4H^-$, $CH_3SO_3^-$, or $AR$-$SO_3^-$; precipitating said anionic organic compounds from said waters as saline derivatives and separating said waters from the precipitate.